US008118158B2

(12) United States Patent
Igota et al.

(10) Patent No.: US 8,118,158 B2
(45) Date of Patent: Feb. 21, 2012

(54) SEALED STORAGE BAG OF MULTIPLE COMPARTMENT STRUCTURE

(75) Inventors: Shoji Igota, Kawasaki (JP); Masayuki Okamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 895 days.

(21) Appl. No.: 11/563,819

(22) Filed: Nov. 28, 2006

(65) Prior Publication Data
US 2007/0084736 A1    Apr. 19, 2007

Related U.S. Application Data

(63) Continuation of application No. PCT/JP2005/009733, filed on May 27, 2005.

(30) Foreign Application Priority Data

May 28, 2004  (JP) .................................. 2004-158607

(51) Int. Cl.
B65D 3/08    (2006.01)
B65D 3/22    (2006.01)
B65D 25/08   (2006.01)

(52) U.S. Cl. .......... 206/221; 206/219; 383/38; 383/116; 426/106; 426/119; 426/120; 428/34.1; 604/403; 604/408; 604/410

(58) Field of Classification Search .................. 426/120, 426/106, 119, 110; 206/219, 221; 383/38, 383/116; 428/34.1; 604/403, 408, 410
See application file for complete search history.

(56) References Cited

U.S. PATENT DOCUMENTS

| 3,808,414 A |   | 4/1974  | Robert |
|-------------|---|---------|--------|
| 5,355,869 A | * | 10/1994 | Pickard et al. ........... 126/263.01 |
| 6,121,597 A |   | 9/2000  | Igota et al. |
| 6,712,201 B1|   | 3/2004  | Bertram |

FOREIGN PATENT DOCUMENTS

| JP | 62-176451   | 1/1986  |
|----|-------------|---------|
| JP | 08-182739   | 7/1996  |
| JP | 10-310181   | 11/1998 |
| JP | 11-020805   | 1/1999  |
| JP | 11-278558   | 10/1999 |
| JP | 2001-146276 | 5/2001  |
| JP | 2002-037278 | 2/2002  |
| JP | 2002-145354 | 5/2002  |

(Continued)

OTHER PUBLICATIONS

Translation of JP 2003-62038A, Onishi et al., Mar. 4, 2003, see Applicant's IDS filed Jun. 24, 2010.*

(Continued)

*Primary Examiner* — Brent O'Hern
(74) *Attorney, Agent, or Firm* — Oblon, Spivak, McClelland, Maier & Neustadt, L.L.P.

(57) ABSTRACT

A sealed storage bag of multiple compartment structure, wherein a separated condition of compartments is needed until just before the use, such as an infusion bag of a mixing type of two kinds of liquid or a bag for cooked storage food with flavoring materials. A sealed storage bag comprises a flexible outer bag; an inner bag as a rectangular small compartment having an inner storage space, which is separated, by a film member, from an outer storage space in the outer bag; a filling port for filling contents; and a discharge port for discharging the contents.

14 Claims, 7 Drawing Sheets

FOREIGN PATENT DOCUMENTS

| | | |
|---|---|---|
| JP | 2002-248158 | 9/2002 |
| JP | 2003-062038 | 3/2003 |
| JP | 2003-159309 | 6/2003 |
| JP | 2003-205014 | 7/2003 |
| JP | 2003-205977 | 7/2003 |
| WO | WO 94/25252 | 11/1994 |

OTHER PUBLICATIONS

Translation of JP 2002-248158, (Isono et al., Sep. 3, 2002, see Applicant's IDS filed Nov. 28, 2006.*

* cited by examiner (a) FRONT VIEW (b) X-X LINE CROSS-SECTION (c) X-X LINE CROSS-SECTION (a) FRONT VIEW (b) X-X LINE CROSS SECTION (c) X-X LINE CROSS SECTION (d) Y-Y LINE CROSS SECTION (a) FRONT VIEW (b) Y-Y LINE CROSS-SECTION (c) X-X LINE CROSS-SECTION (a) FRONT VIEW
(b) X-X LINE CROSS-SECTION
(c) X-X LINE CROSS-SECTION
(d) X-X LINE CROSS-SECTION

SEALED STORAGE BAG OF MULTIPLE COMPARTMENT STRUCTURE

CROSS REFERENCES TO RELATED APPLICATIONS

This application is a continuation of International Patent Application No. PCT/JP05/09733, filed on May 27, 2005, and claims priority to Japanese Patent Application No. 2004-158607, filed on May 28, 2004.

TECHNICAL FIELD

The present invention relates to a sealed storage bag of multiple compartment structure, wherein it has a flexible outer bag for a sealed storage of a content and an inner bag as a small compartment for sealed and separated storage of a content different from the content in the outer bag and wherein, upon usage, the inner bag is, at its wall, broken in a manner that the sealed content in the inner bag and the sealed content in the outer bag are mixed with each other. More particularly, the present invention relates to a sealed storage bag of multiple compartment structure capable of used for a situation that a separated condition should be kept until immediately before the mixture for a usage, such as an infusion bag of double liquid mixture type or a bag for cooked storageable food with flavoring material.

A high calorie liquid for an intravenous infusion for a nutrient care in a medical field such as for a patient after an operation in alimentary system contains a carbohydrate as a nutrient source, an amino acid and an electrolyte. A mixed state of the carbohydrate and the amino may generate a Maillard reaction and, therefore, the storage in the container under a mixed state should not be done. Therefore, for a purpose of storing such a kind of infusion liquids, a type of a container is used, wherein a small compartment is created in the container in a manner that the carbohydrate and the amino-acid are stored under a separate condition and wherein, upon the usage, the small compartment is made a communication with a space inside the container, so that stored liquids are mixed with each other. Thus, a container of this type is proposed, having a flexible bag housing therein with a small compartment separated from the space inside the bag by a portion, which is broken by pressing the bag from its outside (see Patent document 1, Patent document 2 and Patent document 3).

In the above type of container of multiple compartment structure, a setting that the separating part is easily broken is taken when a mixing efficiency during the usage is considered important. However, in this setting, a situation may occur that the separating part is broken by a pressing force applicable outwardly of the bag during its transportation or keeping, resulting in a mixture of liquids separately stored prior to the usage. Contrary to this, in a setting of an increased strength of the separating part for imparting a desired strength, which makes the separating part to oppose to the pressing force, a formation of an opening for making a communication of the small compartment with the space inside the bag during the usage is imperfect, which necessitates a complicated operation for obtaining a desired degree of mixing of the stored liquids.

For combating the above mentioned difficulties that a plurality of contents separately and closely stored in the bag is subjected to an accidental mixing during the transportation or keeping and that a plurality of stored contents is imperfectly mixed due to an insufficient communication between the compartments for storing the contents during the usage, proposed is: a construction of a infusion bag, wherein it has a soft bag for sealed storage of a first liquid and a small container for storing a second liquid, the small container being separated from the soft bag and arranged in one end of the soft bag, the soft bag being subjected to a pressing from its outside in a manner that a breakable part of the small container in the soft bag is broken (see patent document 1) or; a construction of a type of a bag with inner small bag that has a chamber for storing a medical liquid, which suspends therein with a small bag for storing another medial liquid, the small bag being, at a part of its wall, formed with a peelable seal part, which is strongly adhered to an inner wall of the chamber and the seal part is peeled off in a manner that the wall of the small bag is broken when the medical fluid storage chamber is subjected to an pressing from its outside (see patent document 4).

However, these bags are necessarily of a complicated structure, resulting in an increased production cost.

Patent Document 1: Japanese Un-Examined Patent Publication No. S62-176451
Patent Document 2: Japanese Un-Examined Patent Publication No. H08-182739
Patent Document 3: Japanese Un-Examined PCT Publication No. H08-509631
Patent Document 4: Japanese Un-Examined Patent Publication No. 2003-159309
Patent Document 5: Japanese Un-Examined Patent Publication No. 2003-62038

DISCLOSURE OF THE INVENTION

Problem to be Solved by the Invention

The present invention aims to provide a sealed storage bag of multiple compartment structure, wherein the bag has a simplified structure and its production is easy and inexpensive, wherein a mere pressing operation from the outside of the bag during the usage is enough for causing a small chamber (inner bag) in an outer bag to be broken in a manner that a content in the small chamber and a content in the outer bag are mixed, wherein the bag has a sufficient strength capable of bearing any outer pressure applied during the transportation or keeping in a period from the production to the usage, and wherein the bag is formed only from materials, which are not contaminated by and stable to components included in liquids stored in the bag.

Means for Solving the Problem

In order to overcome the above-mentioned problems, the present invention provides a sealed storage bag of multiple compartment structure, wherein it comprises a flexible flat shaped outer bag having an inner storage space and an inner bag in the inner storage space of the outer bag and of a rectangular and flattened compartment separated from the outer bag storage space by a film member, wherein it has a construction that the film member forming said rectangular shaped compartment and one of the walls of the outer bag are connected with each other by means of a welded portion of a small area, wherein, under the condition that the outer bag storage space and inner bag storage space store separately the substances which are to be mixed when being used, the outer bag storage space is pressed from its outside, so that the film member of the compartment (inner bag) is locally broken at said welded portion of small area, thereby causing the storage spaces in the outer and inner bags to be in communication. The present invention may, in particular, be preferably used for a container for infusion wherein vitamins et al, which are unstable when mixed, are separately stored and includes the following claimed inventions.

The invention in claim 1 provides a sealed storage bag of multiple compartment structure, comprising: a flexible outer bag; an inner bag as a rectangular small compartment having an inner storage space, which is separated, by a film member, from an outer storage space in the outer bag; a filling port for filling contents, and; a discharge port for discharging the contents; said inner storage space of the inner bag being formed by welding a peripheral portion of said rectangular film member forming said rectangular compartment to one heat weldable wall (rear wall) of the outer bag; said rectangular film member being, at its middle portion of small area along the width of the rectangular film member, welded to opposed other heat weldable wall (front wall) of the outer bag, so that an inner bag opener portion is created; the contents to be mixed during the use being separately filled, via said filling port, into said outer storage space of the outer bag and said inner storage space of the inner bag, respectively, and being welded and closed, thereby obtaining sealed state, at which state a pressing force applied outwardly at the said outer storage space causes the rectangular film member to be broken at said inner bag opener portion.

The invention in claim 2 provides a sealed storage bag of multiple compartment structure according to claim 1, wherein said inner bag as a rectangular compartment is formed by a single film member, which is folded in two for forming a folded bottom end, side ends and top end, at which ends said inner bag are, along band shaped area, welded to said one wall (rear wall) of the outer bag, thereby forming said inner bag storage space and wherein said the film member is, at the middle portion of a small area along the width thereof, welded to said opposed other wall (front wall) of the outer bag, thereby creating said inner bag opener portion.

The invention in claim 3 provides a sealed storage bag of multiple compartment structure according to claim 1 or 2, wherein said sealed storage bag further comprises a plurality of compartment dividing straight welded portions, extending in parallel from said top welded end to said bottom welded ends of the inner bag in a manner that the rectangular film member constructing the inner bag is welded to said one weldable wall (rear wall) of the outer bag, thereby dividing the inner bag into a plurality of the compartments, said inner bag opener portion being provided for each of said compartments.

The invention in claim 4 provides a sealed storage bag of multiple compartment structure according to claim 3, wherein it further comprises welded portions for reinforcing said inner bag opener portions, said reinforcing welded portions being arranged under an overlapped relationship with respect to said plurality of parallel compartment dividing straight welded portions, said reinforcing portions being constructed by welding said front wall of the outer bag to said straight welded portions at areas extending from said top toward bottom ends of the inner bag for predetermined lengths.

The invention in claim 5 provides a sealed storage bag of multiple compartment structure according to claim 4, wherein the welding of said reinforcing portion to said straight welded portion is such that said reinforcing portion terminates at an upper area with respect to said inner bag opener portion.

The invention in claim 6 provides a sealed storage bag of multiple compartment structure according to any one of claims 1 to 5, wherein said sealed storage bag further comprises a welded portion for assisting the opening of the inner bag opener portion, which is arranged adjacent the inner bag opener portion and which is formed as a non-breakable welded portion extending in the shape of a band along the direction of width at a location above said inner bag opener portion.

The invention in claim 7 provides a sealed storage bag of multiple compartment structure according to any one of claims 1 to 6, wherein said inner bag opener portion comprises a welded portion having angled portion of an acute shape.

The invention in claim 8 provides a sealed storage bag of multiple compartment structure according to any one of claims 1 to 7, wherein said inner bag opener portion is arranged at a middle location along the width of the inner bag and adjacent the bottom end of the inner bag.

The invention in claim 9 provides a sealed storage bag of multiple compartment structure according to any one of claims 1 to 8, wherein said inner bag and said outer bag are constructed by heat weldable film members, having non-absorbing properties to respective materials to be stored in respective storage spaces.

The invention in claim 10 provides a sealed storage bag of multiple compartment structure according to any one of claims 1 to 9, wherein said sealed storage bag further comprises an easily separable welded portion, which divides said outer storage space into vertically spaced two compartments.

The invention in claim 11 provides a sealed storage bag of multiple compartment structure according to any one of claims 1 to 10, wherein said outer bag is formed by a laminated film member including a polyolefine film layer at the inner side and a polyethylene terephthalate film layer at the outer side.

The invention in claim 12 provides a sealed storage bag of multiple compartment structure according to any one of claims 1 to 11, wherein said inner bag is formed by a polyolefine film member.

The invention in claim 13 provides a sealed storage bag for an intravenous infusion product for a total nutrition housed in a container as a multiple compartment type sealed storage bag as claimed in any one of claims 1 to 12, wherein an infusion liquid including saccharides and an infusion liquid including amino-acids are separately stored in said outer storage space of the outer bag and said inner storage space of the inner bag, respectively.

The invention in claim 14 provides a sealed storage bag for a cooked storageable food housed in a container as a multiple compartment type sealed storage bag as claimed in any one of claims 1 to 12, wherein a cooked food and a flavoring material and/or an extra food(s) are separately stored in said outer storage space of the outer bag and said inner storage space of the inner bag, respectively.

Effects of the Invention

The sealed storage bag of multiple compartment structure according to the present invention has a construction, which is capable of formed only by subjecting the heat weldable film for an outer bag and the heat weldable film for an inner bag to a heat welding process. As a result, the structure is simplified, an employment of a mass production system is easy and a reduction of the production cost is possible. Furthermore, a mere pressing operation of the outer bag inner storage space from the outside prior to the use allows the compartment (inner bag) inside the outer bag to be positively broken. In addition, the sealed storage bag is prevented from being accidentally opened by an outside pressure during a process of transportation or keeping from the production to the use.

Furthermore, the sealed storage bag is made from materials, which are of anti-staining properties to substances to be stored. Thus, the present invention is suitable for a container for a medicine of two liquid mixing type, wherein the two kind of liquids must be separately stored until immediately before the use or for a container cooked storageable food, wherein a flavoring material and/or an extra food(s) to be used during a meal or a tea time are/is included.

BRIEF EXPLANATION OF ATTACHED DRAWINGS

EXPLANATION OF REFERENCE NUMERALS

| | |
|---|---|
| 1: | A bag sealed storage bag with multiple compartments |
| 2: | Outer bag |
| 3: | Inner bag |
| 4: | Side end welded portion |
| 5: | Top end welded portion |
| 6: | Inner bag opener portion |
| 7: | Inner bag bottom end welded portion |
| 8: | Outer bag bottom end welded portion |
| 9: | Outlet port |
| 10: | Inner bag opener reinforcing portion |
| 11: | Partition welding portion |
| 12: | Inner bag bottom end |
| 13: | Inner bag opening assist weld portion |
| 14: | Easily separable welded portion |

BEST MODES FOR WORKING THE INVENTION

A sealed storage bag of multiple compartment structure according to the present invention includes an outer bag of a high strength having an outer storage space and an inner bag portion formed as a small compartment having an inner storage space separated from the outer storage space of the outer bag.

In a sealed storage bag of multiple compartment structure according to the present invention, at least the inner part of the outer bag and the entire part of the inner bag are constructed by resin films, which are heat weldable and are of non-absorbency and of flexibility suitable for a purpose for storage of medical products or foods. As film with such non-absorbency and flexibility, polyester film or polyolefin film is preferable, in particular, polyethylene terephthalate film, polyethylene film, polypropylene film or cycloolefine (cop) film or multi-layered film from the foregoing is more preferable. One(s) of the foregoing films, which is (are) of non-absorbency with respect to stored components to be stored, is selected and is used.

Furthermore, in a sealed storage bag of multiple compartment structure according to the present invention, it is required that only the side of film constructing the inner bag wall is positively broken when a separating force is applied to an inner bag opener portion as a welded portion of a small area between the outer and the inner bag. Therefore, it is needed that the synthetic resin film constructing the outer bag has a value of the strength, which is larger than that of the synthetic resin film constructing the inner bag. Thus, in case where the outer bag and the inner bag are formed from the same synthetic resin material, in order to obtain the value of strength of the outer bag higher than that of the inner bag, it is needed that the outer bag has the value of film thickness larger than that of the inner bag. Furthermore, a construction of an outer bag is preferably used, wherein the outer bag is formed from a multi-layer film having a polyolefin as the inner side of the outer bag and a polyester layer for obtaining an increased strength as the outer side of the outer bag.

Now, embodiments of a sealed storage bag of multiple compartment structure according to the present invention will be explained with reference to attached drawings.

Figure 1:
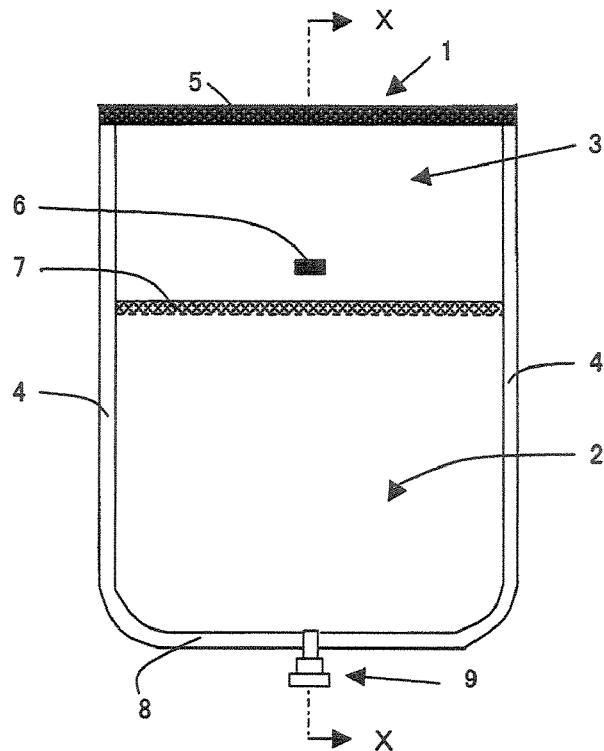
FIG. 1 shows an essential construction of a sealed storage bag of multiple compartment structure according to the present invention and its operating modes.
Figure 1:
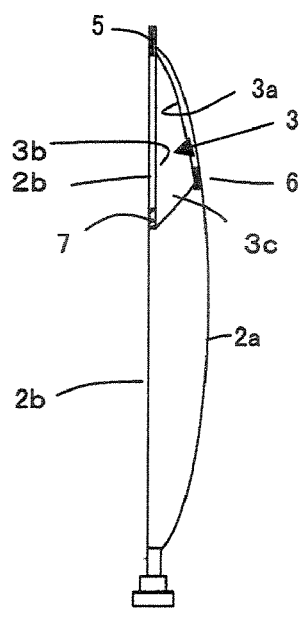
Figure 1:
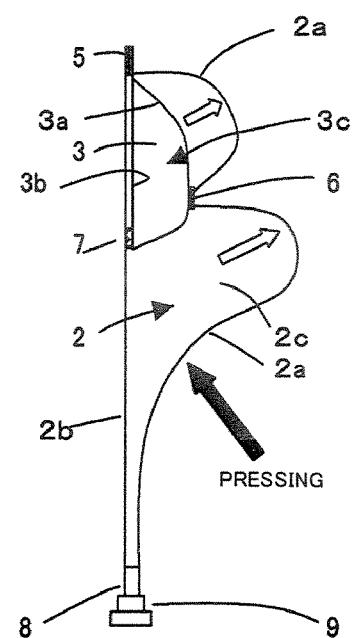

FIG. 1 illustrates a first embodiment of a sealed storage bag of multiple compartment structure according to the present invention, wherein (a) illustrates a front view, (b) illustrates a cross-sectional view taken long line X-X of (a) and (c) illustrates a cross-sectional view taken long line X-X of (a) under a condition that the bag is pressed from its outside in a manner that the outer bag is expanded at a location adjacent the inner bag.

The sealed storage bag of multiple compartment in FIG. 1 is designated by a reference numeral 1 and includes an outer bag 2 and an inner bag 3 housed in a top portion of the outer bag 2 as shown in (a) and (b) of FIG. 1. Arranged at the bottom end of the outer bag 2 is a spout 9 as a discharge port. The sealed storage bag 1 is opened and forms a filling port prior to the introduction of contents.

In the embodiment in FIG. 1, a process for the formation of the outer and inner bags 2 and 3 is as follows. Namely, a synthetic resin film, having, at least its inner side, a heat weldable polymeric layer is folded in two, so that an outer bag part 2 is formed, which has a folded bottom edge, overlapped side edges and a top edge. Inside the synthetic resin film for the outer bag, a synthetic heat weldable resin film of a length shorter than the synthetic resin for the outer bag in the vertical direction is vertically folded in two in a manner that the thus obtained side edges and a top edge of the folded synthetic resin film for the inner bag are overlapped and aligned with the side edges and top edge of the folded synthetic resin film for the outer bag, whereat a heat welding or integration of the heat weldable synthetic resin film for the inner bag 3 to the synthetic resin film for the outer bag 2 is done.

A production of the sealed storage bag of multiple compartment structure in FIG. 1 will now be explained. In an overlapped arrangement of the film for the outer bag and the film for the inner bag as shown in FIGS. 1 (*a*) and (*b*), at the folded portion constructing the bottom end of the inner bag 3, one of walls (rear wall) 3*b* of the film member constructing the inner bag 3 is, along a band like area, welded and connected to one of walls (rear wall) 2b of the outer bag 2, so that an inner bag bottom end welded portion 7 is created. Simultaneously, the other wall (front wall) 3a of the inner bag 3 is welded, at a small area of a rectangular shape, to the other wall (front wall) 2a of the outer bag 2, so that an inner bag opener portion 6 is created. Then, side edge portions of the outer bag film and inner bag film are overlapped and integrally welded, so that side end connected portions 4 of the sealed storage bag 1 is created. Simultaneously, bottom edge portions of the outer bag film are welded, so that an outer bag bottom end welded portion 8 of the sealed storage bag 1 is created.

Thus, the sealed storage bag 1 for sealed storage of multiple compartment structure is obtained, wherein the inner bag 3, which has an inner storage space 3c and the inner bag opener portion 6, is stationary arranged in the outer bag 2, which has an inner storage space 2c.

Finally, both of the storage space 3c of the inner bag 3 and the storage chamber 2c of the outer bag 2 are filled separately by respective materials, which are to be mixed when being used. Furthermore, the filling port as the top open ends are subjected to a heat welding, so that a top end welded portion 5 is created, resulting in a completion of a production of a sealed storage sealed storage bag, such as an intravenous infusion product for a total nutrition housed in a container.

From a condition of a sealed storage bag as shown in FIG. 1(b) as produced, which stores, separately, a plurality of materials to be mixed when being used, the stored portion of the outer bag 2 is pressed upwardly from the bottom as shown by an arrow in FIG. 1(c), so that the upper part of the outer bag housing therein with the inner bag 3 is expanded. A resultant outwardly directed displacement of the front wall 2a of the outer bag 2 is generated, which causes a strong stretching force to be generated at the inner bag opener portion 6, which welds and connects, at a small area, the outer and inner bags with each other. As a result, a breakage of the inner bag opener portion 6 is initiated at its acute angled portions and the thus generated breakage is spreading out, so that the content stored in the inner bag storage area is flown into the space inside the outer bag and is mixed with the content in the outer wall storage space.

Figure 2:
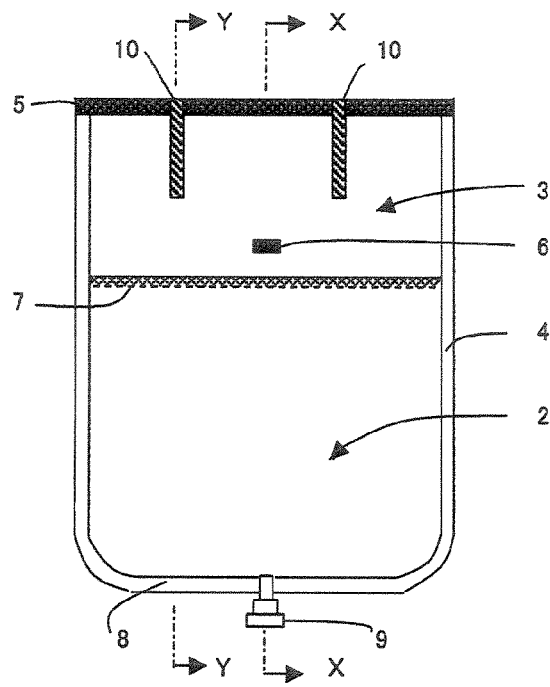
FIG. 2 shows a construction of a sealed storage bag of multiple compartment structure modified from that in FIG. 1 and its modes of operation.
Figure 2:
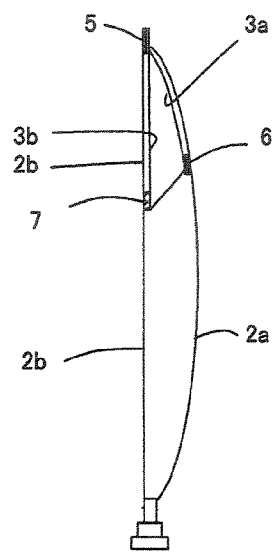
Figure 2:
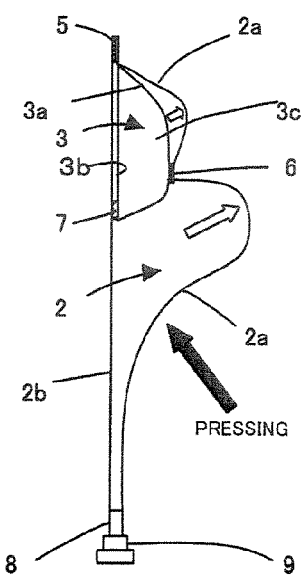
Figure 2:
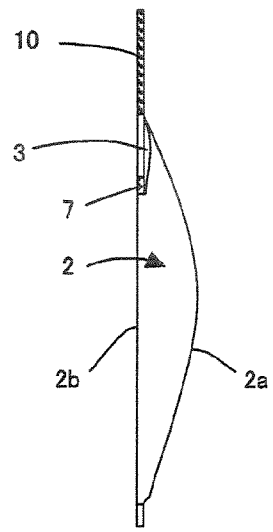

FIG. 2 illustrates a modification of a sealed storage bag in FIG. 1, wherein welded portions 10 for a reinforcement of the inner bag opener portion 6 are added. As shown in FIG. 2(b) and (d), at the upper area of the inner bag opener portion 6 of the inner bag 3, a pair of (two) welded portions 10 for reinforcing the inner bag opener portion, which are arranged in parallel and of band shapes, are provided in a manner that the front wall 2a of the outer bag 2 and the front and rear walls 3a and 3b of the inner bag 3 are welded together to the rear wall 2b of the outer bag 2 and in a manner that the portions 10 extend from the upper end of the sealed storage bag 1 toward the inner bag bottom end welded portion 7 while terminating at the area above the inner bag opener portion 6. By the provision of such reinforcing portions 10, the inner bag 3 is, at its upper part, partitioned and, however, is, at its lower part including the inner bag opener portion 6, opened and communicated.

To a relatively small pressing force inevitably applied to the sealed storage bag 1 as filling and sealing the contents during its transportation or keeping, the outer bag storage space portion 2c is pressed and is subjected to a rapid internal expansion. Even in this case, the reinforcing portions 10 limit an outwardly directed displacement of the front wall 2a of the outer bag 2, so that the inner bag opener portion 6 is prevented from being applied to a rapidly increased stretching force. Thus, the reinforcement, i.e., the protection of the inner bag opener portion 6 prior to the use is obtained.

Figure 3:
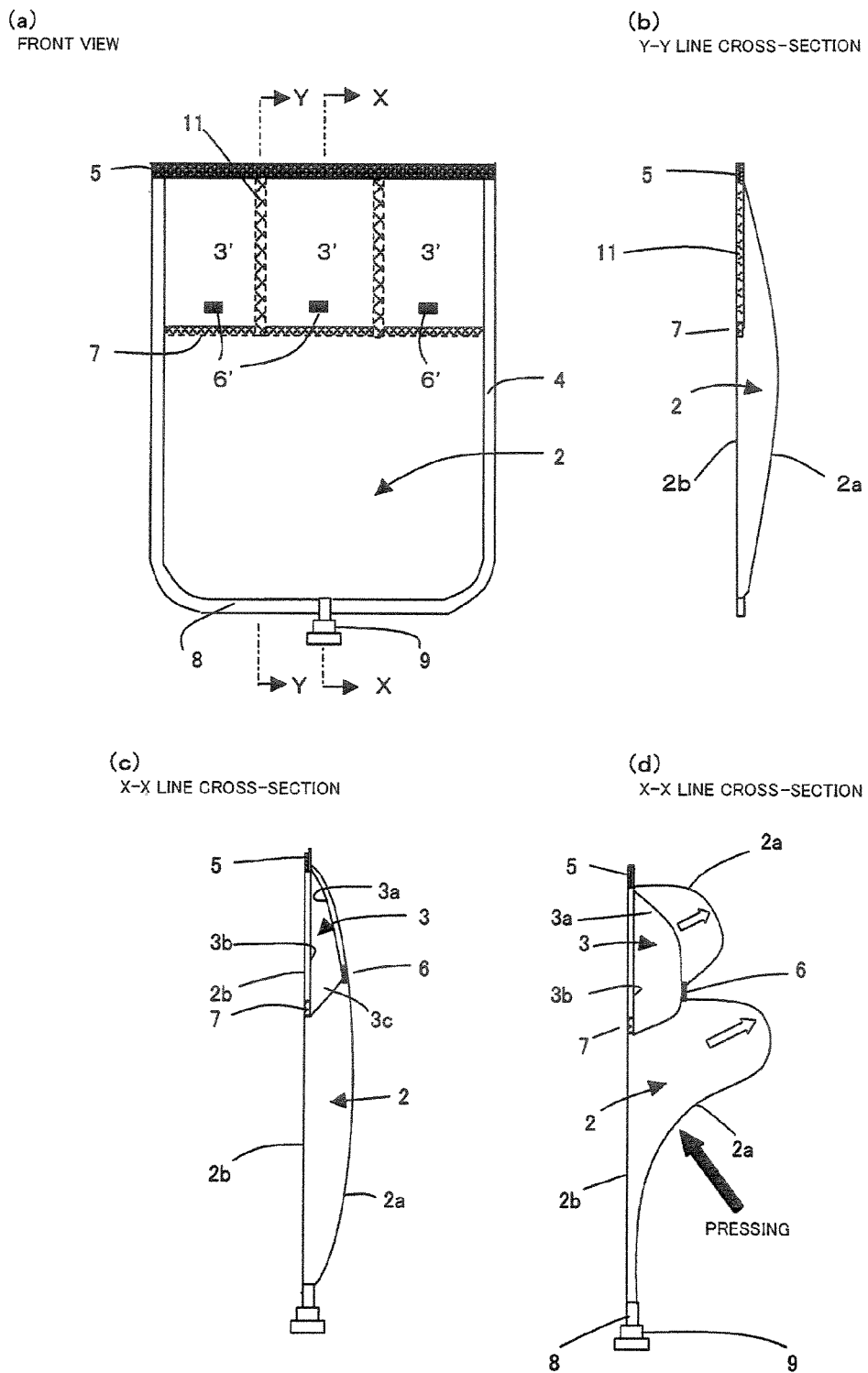
FIG. 3 shows a construction of a sealed storage bag of multiple compartment structure according to the present invention, wherein its inner bag is constructed as a multi-compartment type and its modes of operation.

FIG. 3 illustrates a sealed storage bag 1 for sealed storage of modified construction from that in FIG. 1 in that the inner bag 3 is divided in three. Namely, as shown in FIGS. 3 (a) and (b), the sealed storage bag is provided with a plurality of compartment dividing welded portions 11 of a band shape and extending longitudinally in parallel, by which welded portions the front and rear wall 3a and 3b of the inner bag 3 are welded together to the rear wall 2b of the outer bag 2, so that the inner bag 3 is divided into a plurality of compartments 3', each of which is provided with an inner bag opener portion 6'. As a result, a sealed storage bag is obtained, which is capable of separately storing materials of much more varieties. In FIG. 3, a cross-sectional view taken along the line X-X in (a) is shown in (c), a cross-sectional view taken along the line Y-Y is shown in (c) and a condition of a part of the sealed storage bag adjacent the inner bag opener portion 6' when expanded by a pressing of the outer bag storage space 2c is shown in (d).

Figure 4:
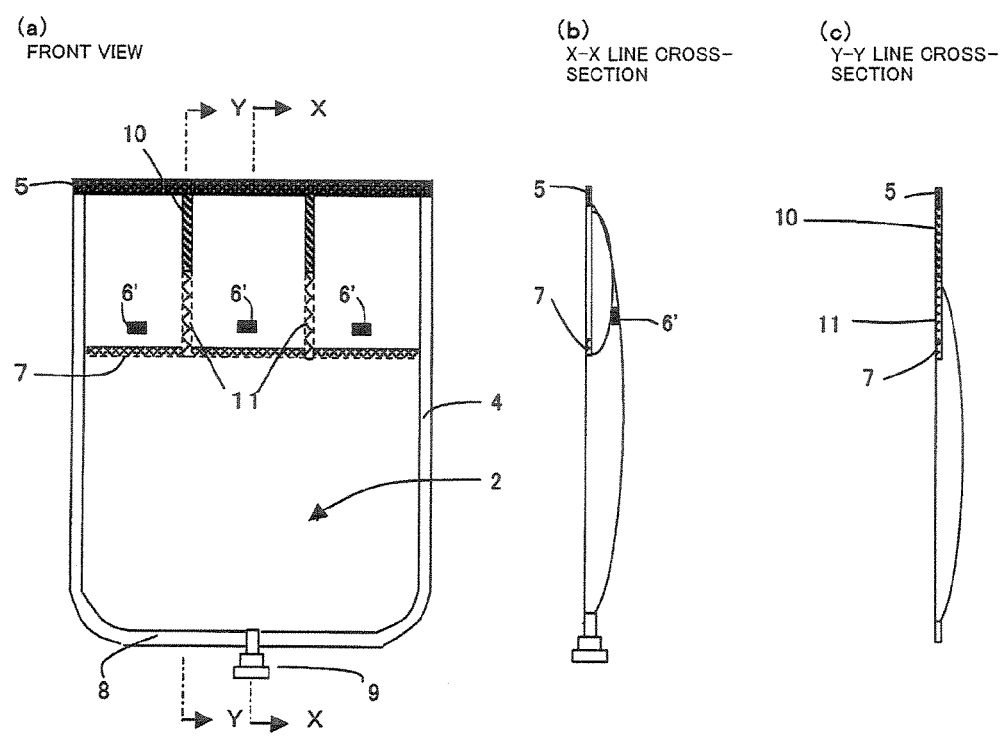
FIG. 4 shows a construction of a sealed storage bag of multiple compartment structure modified from that in FIG. 3 and its modes of operation.

FIG. 4 illustrates an embodiment of a sealed storage bag 1 for sealed storage modified from that in FIG. 3 in that a pair of reinforcing welded portions 10 of the inner bag opener portions are provided on the respective compartment dividing welded portions 11 dividing the inner bag into compartments 3' in a manner that the reinforcing welded portions 10 extend from the upper ends to the bottom ends of the respective partitions 3' and terminate at locations upstream from the inner bag opener portions 6'.

In case of the sealed storage sealed storage bag in FIG. 4, the reinforcing welded portions 10 are formed by welding the front wall 2a of the outer bag 2 along a band shaped area of a predetermined length in a manner that the portions 10 are overlapped with the compartment dividing welded portions 11, which extend, in parallel, along a band shaped area in the longitudinal direction and divide the inner bag 3 into the partitions, as shown in FIGS. 4 (a), (b) and (c). The arrangement of the reinforcing welded portions 10 as shown in FIG. 4 is desirable in case of a sealed storage bag where each of the partitions 3' is of a small size as shown in FIG. 3 due to the increased number of the varieties of the materials to be separately stored.

In the sealed storage bags as shown in above figures, it is desirable that the inner bag opener portion 6 is arranged at a location adjacent the inner bag bottom end welded portion 7 in the inner bag 3. Such an arrangement of the inner bag opener portion 6 can reduce a moving distance of the inner bag opener portion 6 as stretched by the movement of the outer wall of the outer bag moved outwardly by the expansion of the outer bag when an expansion force is applied to the outer bag at a location adjacent the inner bag opener portion due to the compression force from lower side of the outer bag, resulting in a concentrated application of a strong stretching force to the inner bag opener portion 6 from the initial phase of the expansion of the outer bag storage space. As a result, a positive breakage of the inner bag opener portion is obtained, on one hand and, on the other hand, a complete discharge of the content in the inner bag after the breakage of the inner bag opener portion is obtained.

Figure 5:
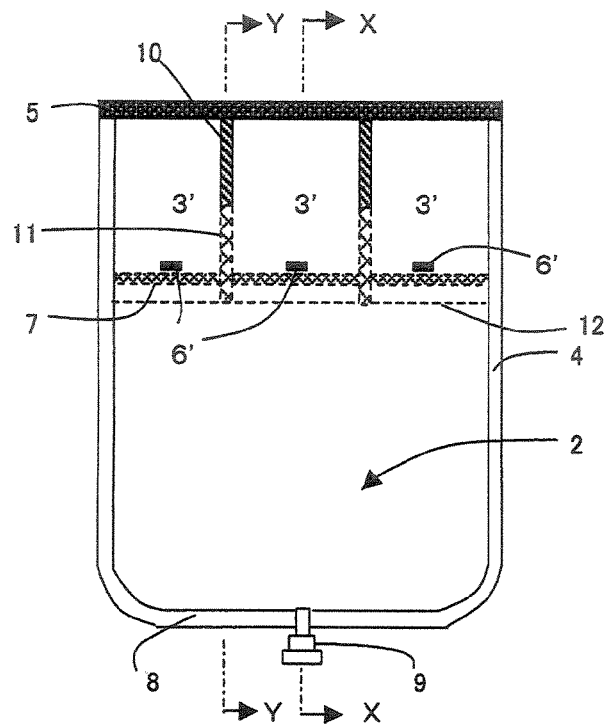
FIG. 5 shows a construction of a sealed storage bag of multiple compartment structure modified from that in FIG. 4 and its modes of operation.
Figure 5:
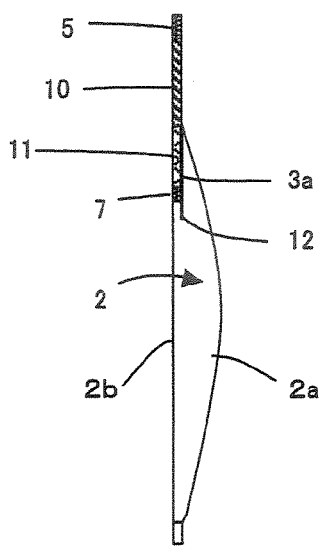
Figure 5:
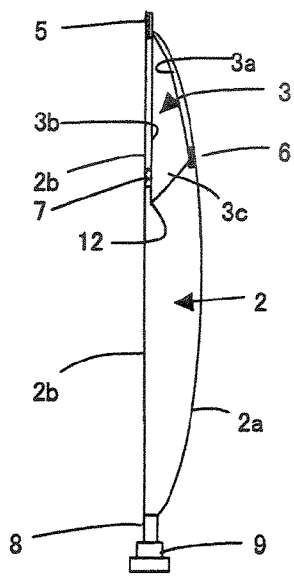

An embodiment of a sealed storage bag in FIG. 5 is modified from that in FIG. 4, in that an inner bag bottom end welded portion 7 at a bottom portion of the inner bag 12 is spaced from the bottom end 12 of the inner bag 3. By such a separation of the inner bag bottom end welded portion 7 from the bottom edge 12, a free end portion is created at the bottom end of the inner bag 3. In case of an expansion of the outer bag due to a pressing of the outer bag during a transportation or keeping of a sealed storage sealed storage bag, the free end portion prevents the pressing force, which is relatively small, from being directly applied to the inner bag opener portion 6'. This embodiment is advantageous when a strengthening function of the inner bag opener portion is considered important.

Figure 6:
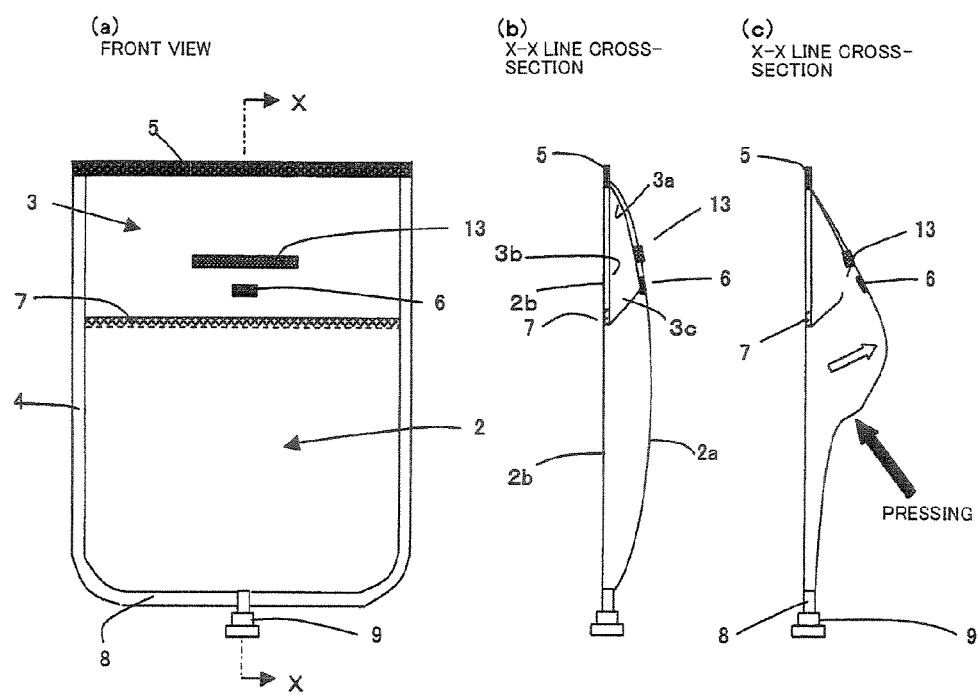
FIG. 6 shows a construction of a sealed storage bag of multiple compartment structure modified from that in FIG. 1 in that an inner bag opening assisting welded portion is provided and its modes of operation.

FIG. 6 is a modified embodiment of a sealed storage bag, wherein a welded portion 13 is provided at a location adjacent the inner bag opener portion 6 for assisting the opening thereof. As shown in FIGS. 6(*a*) and 6(*b*) as a cross-sectional view taken along line X-X in FIG. 6(*a*), the inner bag opening assist portion 13 is formed by a non-breakable welded portion of an increased width, which connects the front wall 3*a* of the inner bag and the front wall 2*a* of the outer bag and which is located at a position adjacent the inner bag opener portion 6 of a small area having a acute angle portion. Due to the provision of such a inner bag opening assist welded portion 13, after the breakage of the inner bag opener portion 6 under the outer pressure applied to outer bag 2, the broken portion is additionally stretched and widened by the welded portion 13, resulting in a positive removal of the content stored in the inner bag 3. The sealed storage bag having such an inner bag opening assist welded portion 13 is advantageous for a usage for a cooked storageable food, wherein the content in the inner bag is generally of a inferior in the flowability. A modification is possible where an inner bag opening assist welded portion 13 is arranged so as to be adjoining to the upper side of the inner bag breaker portion.

Figure 7:
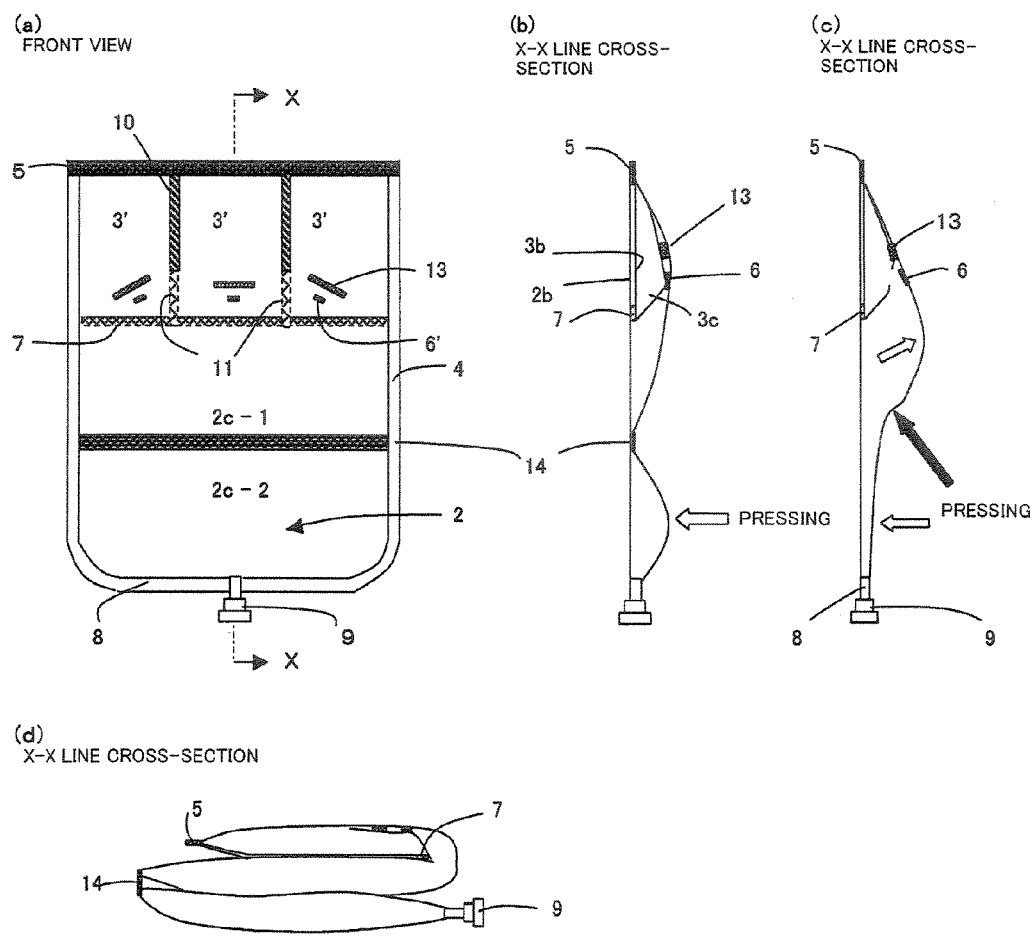
FIG. 7 shows a construction of a sealed storage bag of multiple compartment structure modified from that in FIG. 4, wherein inner bag opening assisting welded portions and an easy separatable welded portion in an outer gag are added and its modes of operation.

FIG. 7 illustrates a modified sealed storage sealed storage bag 1, wherein it includes a opening assist welded portion 13 for an inner bag opener portion and an easily separable welded portion 14, which divides, vertically, the storage space of the inner bag into storage spaces 2*c*-1 and 2*c*-2.

Such an easily separable welded portion 14 is obtained by a head welding of heat the weldable layers inside an outer bag 2 at a reduced heat welding temperature. During the use, the portion 2*c*-2 is pressed as shown by an arrow in FIG. 7(*b*), resulting in a breakage of the easily separable welded portion 14, so that the portion 2*c*-2 is made communication with the portion 2*c*-1. The bag is subsequently pressed as shown by an arrow in FIG. 7(*c*), which causes the inner bag opener portion to be broken, resulting in a mixture of all the contents.

A Z-shaped folded structure of the sealed storage bag of this embodiment can be obtained by folding it about the easily separable welded portion 14 and the inner bag bottom end welded portion 7 as shown in FIG. 7(*d*). This folded arrangement is advantageous in that the inner bag opener potion 6 is prevented from being directly subjected to an increased breaking force when an increased pressing force is accidentally applied to the sealed storage sealed storage bag during its transportation or keeping.

In reference to each of the forgoing embodiments with reference to the respective figures, it has been explained that the inner bag is formed from a single film member folded in two. However, the inner bag may be formed from a single film, which is directly welded to the front and rear walls of the outer bag.

DESCRIPTION OF EXAMPLES

Now, the invention will be practically explained with reference to examples of sealed storage bags. However, modifications and changes of these examples can be made without departing scope and sprit of the present invention and are included in the present invention.

Example 1

A lamination of a polyester film of thickness of 12 μm, urethane based adhesive of 3.5 g/m² by TOYO MORTON Ltd. in the trade name of AD-900 and L-LEPE film of thickness of 70 μm by TOHCELLO Co. in the trade name of TUX-FCS is done under a dry laminate method, so that a wrapping material of width of 130 mm and of a length of 400 mm for a size of outer bag of width of 130 mm and of a length of 200 mm was obtained. Furthermore, from L-LDPE (liner low density polyethylene) film of thickness of 30 μm by TOHCELLO Co. in the trade name of TUX-FCS, a wrapping material of width of 130 mm and of a length of 140 mm for a size of inner bag of width of 130 mm and of a length of 70 mm was obtained.

Next, the outer bag wrapping material and the inner bag wrapping material were, at their longitudinal ends, overlapped and were folded in two while the inner bag wrapping material being located inside, and the first wall (rear wall) of the inner bag wrapping material was welded to the first wall (rear wall) of the outer bag wrapping material by using an impulse type sealing machine by FUJIIMPULSE Co., LTD in the trade name of OPL-300-10, for obtaining the inner bag bottom end welded portion 7 as shown in FIG. 7. Thus, a size of inner bag portion 3 of width of 130 mm and of a length of 70 mm was obtained. Then, by using a heat seal machine from TESTER SANGYO Co., LTD., with the seal bar modified, a rectangular shaped portion of area of 4.5 mm×4.5 mm at the center of the width of the second wall (front wall) 3*a* of the inner bag wrapping material at a distance of 12 mm upwardly from the folded portion of the inner bag portion 3 was welded to the second wall (front wall) 2*a* of the outer bag wrapping material, so that an inner bag opener portion 6 is obtained. Then, as shown in FIG. 1, the side end portions of the outer bag wrapping material were welded to obtain the side end welded portions 4 of the sealed storage bag 1 and the folded end portions of the outer bag wrapping material were welded to obtain the bottom end welded portion 8 of the sealed storage bag. Thus, a sealed storage sealed storage bag 1, having an outer bag 2 and an inner bag 3 housed in the outer bag 2 at its upper part, was obtained.

The thus obtained sealed storage bag has a construction that, inside the outer bag 2, the inner bag 3 is, at the band shaped area along the bottom end (the folded portion of the inner bag wrapping material), welded to the rear wall 2*b* and the inner bag front wall 3*a* is, at the portion of area of 4.5 mm×4.5 mm at the center of the width, welded to the outer bag front wall 2*a*, so that the inner bag opener portion 6 is created, and that, at the upper end of the sealed storage sealed storage bag 1, both of the inner and outer bags for openings for filling the respective contents.

Next, a separate spout 9 for a discharge of the content was mounted to the bottom 8 of the sealed storage sealed storage bag 1 as produced above. Thus, a production of the sealed storage sealed storage bag 1 was completed.

A red colored water of 15 ml as a dummy liquid was introduced into the storage space 3*c* of the inner bag 3 via a filling port at the top end of the sealed storage sealed storage bag 1 as produced above and a water of 150 ml was introduced into the storage space 3*c* of the inner bag 3, and that the upper filling port was welded and closed for forming the top end welded portion 5, so that a sealed storage sealed storage bag storing separately therein with two kinds of liquids and having configuration as shown in FIG. 1(*b*) as a cross-sectional view of FIG. 1(*a*) along line X-X in FIG. 1(*a*) was obtained.

Next, a test by using Tensilon type compression tester was done for 30 copies of the sealed storage sealed storage bag 1 as produced above, wherein the outer bag was, at its outside, pushed by a pressing tool of a diameter of 100 mm from its bottom toward the center in a horizontal direction so as to concentrate the resultant inner pressure of the outer bag storage space 2c in the upward direction as shown in FIG. 1(c) and a condition of the breakage of the inner bag opener portion 6 and a condition of mixture of the red colored water in the inner bag with the water in the outer bag were observed.

At pushing pressure of 15N, the inner bag opener portions 6 of all of the sealed storage bags 1 were broken, resulting in a discharge of the red colored water as stored and a mixture thereof with the water stored in the outer bag.

Example 2

A sealed storage sealed storage bag 1 having an outer bag and an inner bag stored in the outer bag at its upper portion was produced in the same way as described with reference to the Example 1.

Next, at a position above the inner bag opener portion in the upper part of the outer bag 2 storing the inner bag, the outer bag front wall 2a, the inner bag front wall 3a, the inner bag rear wall 3b and the outer bag rear wall 2b were integrally welded along a pair of band shaped welded portion of a width of 6 mm and of length 40 mm and extending from the upper end of the sealed storage bag 1 toward the inner bag bottom end welded portion 7, thereby forming welded portions 10 for a reinforcement of the inner bag opener portion 6.

In the thus obtained sealed storage sealed storage bag 1, in the same way as explained with reference to the Example 1, an introduction of the red colored water into the inner bag storage space 3c and an introduction of the water into the outer bag storage space 2c were done and the upper opening of the sealed storage bag was welded and closed in order to form the top end welded portion 5, so that a sealed storage sealed storage bag for a separate storage of two kinds of contents having the cross-sectional shape as shown in FIG. 2(c) was obtained.

Next, a test by using Tensilon type compression tester was done for 30 copies of the sealed storage sealed storage bag 1 as produced above, wherein the outer bag was, at its outside, pushed by a pressing tool of a diameter of 100 mm from its bottom toward the center in a horizontal direction so as to concentrate the resultant inner pressure of the outer bag storage space 2c in the upward direction as shown in FIG. 2(c) and a condition of the breakage of the inner bag opener portion 6 and a condition of mixture of the red colored water in the inner bag with the water in the outer bag were observed.

At pushing pressure of 20N, the inner bag opener portions 6 of 30 copies of the sealed storage sealed storage bag 1 were completely broken, resulting in a discharge of the red colored water as stored and a mixture thereof with the water stored in the outer bag. At pushing pressure of 20N, the inner bag opener portions 6 of 7 copies of the sealed storage sealed storage bag 1 were not broken or imperfectly broken.

In view of the above, it will be understood that the provision of the reinforcing portion 10 for the inner bag opener portion 6 as shown in FIG. 2 is effective for preventing a premature mixture of the stored liquids from being occurred under a relatively small pushing pressure inevitably generated in a sealed storage bag during its transportation or keeping.

Example 3

A sealed storage sealed storage bag 1 having an inner bag divided into three compartments as shown in FIG. 3 was produced under the following procedures by using an outer bag wrapping material and an inner bag wrapping material made from the same material and of the same size as used in the Example 1 and by using an impulse type sealing machine by FUJIIMPULSE Co., LTD in the trade name of OPL-300-10 and a heat seal machine from TESTER SANGYO Co., LTD., which is the same as used in the Example 1.

The outer bag wrapping material and the inner bag wrapping material were, at their longitudinal ends, overlapped and were folded in two while the inner bag wrapping material being located inside, and the rear wall of the inner bag wrapping material was, at a band shaped area along the folded end of the inner bag wrapping material, welded to the rear wall of the outer bag wrapping material, thereby forming the inner bag bottom end welded portion 7 as shown in FIG. 3. Simultaneously, the inner bag front wall 3a was welded to the outer bag front wall 2a at areas of 4.5 mm×4.5 mm located at the center along the width in the respective sections as evenly divided in three along the width of the inner bag wrapping material and located upwardly from the inner bag folded portion at a distance of 12 mm, thereby forming inner bag opener portions 6' at the three locations.

Next, the inner bag front wall 3a and the outer bag front wall 2a were integrally welded to the outer bag rear wall 2b along a pair of compartment welded portions 11 extending in parallel from the opened end of the inner bag to the inner bag bottom end welded portion 7 so as to cause the three inner bag opener portions 6' to be located at the respective center along the width, thereby forming the inner bag 3 comprised of three compartments 3'.

Next, the outer bag side ends 4 and the bottom end were welded and closed, thereby obtaining a sealed storage bag having an outer bag 2 and an inner bag housed in the outer bag at its upper part and comprised of three compartments 3' as shown in FIG. 3.

Next, a separate spout 9 for a discharge of the content was mounted to the bottom 8 of the sealed storage sealed storage bag 1 as produced above, thereby obtaining the sealed storage sealed storage bag 1 as shown in FIG. 3.

A red colored water of 5 ml as a dummy liquid was introduced into the each of the three storage spaces 3' via the filling opening at the top of the sealed storage sealed storage bag 1 as obtained and a water of 150 ml was introduced into the storage space 2c of the outer bag 2. After that, the upper filling port was welded and closed for forming the upper end welded portion 5. Thus, a sealed storage bag having four chambers for storing therein with respective contents was produced.

Next, a test by using Tensilon type compression tester was done for 30 copies of the sealed storage sealed storage bag 1 as produced above, wherein the outer bag was, at its outside, pushed by a pressing tool of a diameter of 100 mm from its bottom toward the center in a horizontal direction and a condition of the breakage of the inner bag opener portion 6 and a condition of mixture of the red colored water in the inner bag with the water in the outer bag were observed.

At pushing pressure of 15N, the inner bag opener portions 6 of all of the sealed storage bags 1 were broken, resulting in a discharge of the red colored water as stored and a mixture thereof with the water stored in the outer bag.

Example 4

In the similar way as described with reference to the Example 3, a sealed storage sealed storage bag 1 having therein with an inner bag 3 comprised of three compartments 3' as shown in FIGS. 4(a) and (b) was produced. Then, on the welded portions 11 for obtaining divided three compartments 3', a welding of the outer bag front wall 2a to the welded portions 11 was done at areas extending downwardly from the open end of the bag at lengths of 20 mm, 30 mm and 60 mm, thereby obtaining the welded portions 10 for a reinforcement of the inner bag opener portion 6. It should be noted that the length of the reinforcing welded portion 10 of a length of 60 mm indicates that the welding of the outer bag front wall is done along the entire length of the welded portion 11.

A test by using Tensilon type compression tester was done for 30 copies of the sealed storage sealed storage bag 1 as produced above, wherein the outer bag was, at its outside, pushed by a pressing tool of a diameter of 100 mm from its bottom toward the center in a horizontal direction and a condition of mixture of the red colored water in the inner bag with the water in the outer bag were observed. The result is shown in Table 1 below.

Example 5

A sealed storage sealed storage bag 1 as shown in FIG. 5 was obtained in the similar way as explained with reference to FIG. 4 except that the band shaped bottom end welded portion 7 welding the bottom ends of the three compartments 3' in the inner bag 3 was arranged in parallel with and at a distance of 12 mm upstream from the folded end of the inner bag wrapping material forming the inner bag 3 and that the reinforcing portions 10 for the inner bag opener portions on the welded portion 11 dividing the three compartments 3' had the length of 35 mm. In the similar way as explained with reference to FIG. 4, for 30 copies of the sealed storage sealed storage bag 1, the outer bag was, at its outside, pushed by a pressing tool of a diameter of 100 mm from its bottom toward the center in a horizontal direction and a condition of the breakage of the inner bag opener portions 6 of three compartments 3' and a condition of mixture of the red colored water in the inner bag with the water in the outer bag were observed. The result is shown in the following Table 1.

TABLE 1

| Sample | Size in mm of Front Seal portion | Position of folded portion | Success Rate of Breakage (%) | Pushing pressure (N) |
| --- | --- | --- | --- | --- |
| a | 6 × 20 | Below | 100 | 10 |
| b | 6 × 30 | Below | 100 | 20 |
| c | 6 × 60 | Below | 70 | 50 |
| d | 6 × 35 | 10 mm Above | 100 | 25 |

Tester Used: Tensilon Tester of ex Toyo Baldwin Co. Ltd.
Pushing Speed: 50 mm/min.

As will be understood from the Table 1, the sealed storage sealed storage bag 1 having an inner bag opener portion 6 can store contents separately with each other in the sealed storage bag until the usage and the means separating with each other in the sealed storage bag can be broken merely by a pushing pressure from the outside just before the usage. Furthermore, the provision of the reinforcing welded portion 10 for the inner bag opener portion 6 can provide a stable strength to the pushing pressure which is inevitably applied to the sealed storage sealed storage bag during its transportation or keeping. In case of the sample c of the reinforcing welded portion 10 of a length of 60 mm, the success rate of the breakage (opening) is 70%. However, an additional manual application of expansion force concentrated at the inner bag opener portion can easily complete the breakage. In case of the sample c, due to the size of the bag used in the test, a relatively large number of missed breakage was generated. However, an increased size of the bag causes the size of an inner bag compartment to be correspondingly increased, by which an increased strengthening effect of the inner bag opener portion can be expected.

The result of the example 5 shows, also, that the arrangement of the bottom end welded portion 7 of the inner bag 3 located slightly above the bottom end of the inner bag can provide a stable strength to a pushing pressure inevitably applied to the sealed storage sealed storage bag during its transportation or keeping.

Example 6

In the sealed storage sealed storage bag 1 in the Example 5 (b) at locations adjacent the inner bag opener portions of the respective three compartments 3' of the inner bag 3, inner bag opening assist welded portions 13 for the inner bag opener portions 7 were provided by welding the inner bag front wall 3*a* and the outer bag front wall 2*a* and an easily separable welded portion 14 was provided for dividing vertically the inner storage space 2 of the outer bag 2, thereby producing the sealed storage bag of a construction as shown in FIG. 7

A red colored water was filled to the each of the compartments construction the inner bag of the sealed storage sealed storage bag via the opening at the top end of the bag, a water was then filled to the compartment 2*c*-1 divided by easily separable welded portion 14 in the outer bag storage space 2*c* via a spout, and the upper opening of the bag was finally welded and closed for forming the top end welded portion 5, thereby producing the sealed storage sealed storage bag as shown in FIG. 7(*a*).

The Z-shaped folded structure as shown in FIG. 7(*d*) in this sealed storage bag is effective for preventing an accidental occurrence of the breakage of the inner bag opener portion 6 during the transportation or keeping.

Furthermore, during the use of the sealed storage bag, the outer bag bottom side 2*c*-1 was pressed outwardly as shown by an arrow in FIG. 7(*b*) in a manner that the easily separable welded portion 14 separating in two the outer bag storage space 14 was separated, so that the stored liquids in the sections 2*c*-1 and 2*c*-2 were easily combined. Then, as shown in FIG. 7(*c*), the outer bag was, as a whole, pressed outwardly for opening the three inner bag opener portions 7, thereby causing the red colored water in the inner bag to be mixed with the water in the outer bag.

APPLICABILITY IN INDUSTRIES

The sealed storage bag of multiple compartment structure according to the present invention may be widely used for pharmaceuticals or storageable foods of a type that contents are separately stored during its transportation or keeping and that the contents are mixed just before usage. In addition, the present invention may be applied to various fields where a container for storing plurality of mutual reactive substances, which are required to be separately stored until the use, is needed.

The invention claimed is:
1. A sealed storage bag, comprising:
an outer bag;
an inner bag provided within the outer bag; and
a discharge port that communicates between an interior of the outer bag and an exterior of the storage bag;
wherein:
the outer bag comprises a substantially rectangular front film wall and a substantially rectangular rear film wall;
the inner bag comprises a substantially rectangular front film wall and a substantially rectangular rear film wall;

top edges of the outer bag front film wall, the outer bag rear film wall, the inner bag front film wall, the inner bag rear film wall are welded together at a top edge of the storage bag;

bottom edges of the outer bag front film wall and the outer bag rear film wall are welded together at a bottom edge of the storage bag;

first side edges of the outer bag front film wall and the outer bag rear film wall are welded together at a first side edge of the storage bag;

second side edges of the outer bag front film wall and the outer bag rear film wall are welded together at a second side edge of the storage bag;

first side edges of the inner bag front film wall and the inner bag rear film wall are welded together with the first side edges of the outer bag front film wall and the outer bag rear film wall at an upper portion of the first side edge of the storage bag;

second side edges of the inner bag front film wall and the inner bag rear film wall are welded together with the second side edges of the outer bag front film wall and the outer bag rear film wall at an upper portion of the second side edge of the storage bag;

a bottom edge of the inner bag rear film wall is welded to the outer bag rear film wall;

an opener portion of the inner bag front film wall is welded to the outer bag front film wall;

the opener portion of the inner bag front film is separated from the top edge, first side edge, second side edge, and a bottom edge of the inner bag front film, but adjacent to the bottom edge of the inner bag front film; and when the outer bag and the inner bag are filled, application of a compression force to the outer bag causes the inner bag front film wall to rupture in proximity to the opener portion of the inner bag front film wall and the contents of the outer bag and the inner bag to mix.

2. The sealed storage bag of claim 1, wherein the inner bag front film wall and the inner bag rear film wall are formed from a single film member folded in two, the fold being provided at the bottom edge of the inner bag front film wall and the inner bag rear film wall.

3. The sealed storage bag of claim 2, wherein:
the inner bag front film wall is welded to the inner bag rear film wall by a plurality of substantially vertical welds extending from the top edge of the inner bag front film wall and the inner bag rear film wall to the bottom edge of the inner bag front film wall and the inner bag rear film wall, the substantially vertical welds separating the inner bag into a plurality of compartments;

the opener portion is provided on a portion of the inner bag front film wall forming a first of the plurality of compartments;

at least one additional opener portion of the inner bag front film wall is welded to the outer bag front film wall; and the at least one additional opener portion is provided on a portion of the inner bag front film wall forming each of a remainder of the plurality of compartments.

4. The sealed storage bag of claim 3, wherein:
the outer bag front film wall is welded to the inner bag front film wall at reinforcing portions corresponding to each of the plurality of substantially vertical welds; and the reinforcing portions extend along at least a portion of each of the plurality of substantially vertical welds including a top edge of each of the plurality of substantially vertical welds.

5. The sealed storage bag of claim 4, wherein the reinforcing portions terminate above a location of the opener portions.

6. The sealed storage bag of claim 1, wherein:
an assist portion of the inner bag front film wall is welded to the outer bag front film wall; and the assist portion of the inner bag front film is separated from the top edge, first side edge, second side edge, and bottom edge of the inner bag front film, and provided above the opener portion.

7. The sealed storage bag of claim 1, wherein the opener portion comprises a welded portion having an angled portion of an acute shape.

8. The sealed storage bag of claim 1, wherein the opener portion is provided substantially centrally with respect to the first side edge and the second side edge of the inner bag front film.

9. The sealed storage bag of claim 1, wherein:
the inner bag comprises a material that is heat-weldable and does not absorb a material stored in the inner bag; and the outer bag comprises a material that is heat-weldable and does not absorb a material stored in the outer bag.

10. The sealed storage bag of claim 1, wherein the outer bag front film wall and the outer bag rear film wall are welded together at an easily separable welded portion that separates the outer bag into two compartments.

11. The sealed storage bag of claim 1, wherein:
each the outer bag front film and the outer bag rear film comprises a laminate;

the laminate comprises a polyolefin film layer at a polyethylene terephthalate film layer;

the polyolefin film layer is adjacent to the interior of the outer bag in each of the outer bag front film and the outer bag rear film; and the polyethylene terephthalate film layer is adjacent to an exterior of the outer bag in each of the outer bag front film and the outer bag rear film.

12. The sealed storage bag of claim 1, wherein each the inner bag front film and the inner bag rear film comprises a polyolefin film member.

13. The sealed storage bag of claim 1, wherein:
an infusion liquid including saccharides is stored in the outer bag; and an infusion liquid including amino-acids is stored in the inner bag.

14. The sealed storage bag of claim 1, wherein:
a cooked food is stored in the outer bag; and a flavoring material and/or an extra food(s) is stored in the inner bag.

* * * * *